United States Patent [19]
Chen et al.

[11] Patent Number: 5,814,008
[45] Date of Patent: *Sep. 29, 1998

[54] METHOD AND DEVICE FOR APPLYING HYPERTHERMIA TO ENHANCE DRUG PERFUSION AND EFFICACY OF SUBSEQUENT LIGHT THERAPY

[75] Inventors: James C. Chen, Bellevue, Wash.; Brent Wiscombe, Mesa, Ariz.

[73] Assignee: Light Sciences Limited Partnership, Issaquah, Wash.

[ * ] Notice: The term of this patent shall not extend beyond the expiration date of Pat. No. 5,445,608.

[21] Appl. No.: 688,058

[22] Filed: Jul. 29, 1996

[51] Int. Cl.⁶ ....................................................... A61N 1/30
[52] U.S. Cl. ............................... 604/21; 604/49; 604/113; 604/114; 607/88; 607/89; 607/98; 607/99
[58] Field of Search .................................. 604/19–22, 49, 604/113, 114; 607/88–89, 98, 99

[56] References Cited

U.S. PATENT DOCUMENTS

| | | | |
|---|---|---|---|
| 4,556,057 | 12/1985 | Hiruma et al. | 604/20 |
| 4,822,335 | 4/1989 | Kawaii et al. | 604/20 |
| 4,932,934 | 6/1990 | Dougherty et al. | |
| 4,957,481 | 9/1990 | Gatenby | 604/20 |
| 5,066,291 | 11/1991 | Stewart . | |
| 5,257,970 | 11/1993 | Dougherty | 604/20 |
| 5,405,369 | 4/1995 | Selman et al. | 604/20 |
| 5,445,608 | 8/1995 | Chen et al. | 604/21 |
| 5,482,719 | 1/1996 | Guillet et al. | 424/486 |
| 5,490,840 | 2/1996 | Uzgiris et al. | 604/22 |

OTHER PUBLICATIONS

Nah, Byung Sik, M.D. et al., "Vascular Thermal Adaptation in Tumors and Normal Tissue in Rats," Int. J. Radiation Oncology Biol. Phys., vol. 35, No. 1, pp. 95–101, 1996; © 1996 Elsevier Science Inc.

Schuster, J.M., et al., "Hyperthermic modulation of radio-labelled antibody uptake in a human glioma xenograft and normal tissues," Int. J. Hyperthermia, 1995, vol. 11, No. 1, © 1995 Taylor & Francis Ltd., pp. 59–72.

Dewhirst, M.W., "Future directions in hyperthermia biology," Int. J. Hyperthermia, 1994, vol. 10, No. 3, © 1994 Taylor & Francis Ltd., pp. 339–345.

Ma, L.W., et al., "Effects of Light Exposure on the Uptake of Photofrin II in Tumors and Normal Tissues," Int. J. Cancer: 52, 120–123 (1992), © 1992 Wiley–Liss, Inc., Publication of the International Union Against Cancer, 4pp.

Yatvin, Milton B. et al., "Design of Liposomes for Enhanced Local Release of Drugs by Hypethermia," Science, vol. 202, 22 Dec. 1978, © 1978 AAAS, 2pp.

*Primary Examiner*—Mark Bockelman
*Attorney, Agent, or Firm*—Ronald M. Anderson

[57] ABSTRACT

A method and apparatus for applying beat to a treatment site prior to effecting photodynamic therapy. The perfusion of a drug into abnormal tissue in a tumor (12) is enhanced by heating the treatment site at which the tumor is disposed using a heat source (26) mounted on a fixture (20, 34) separate from a light source (28) on a probe used to effect the photodynamic therapy. Alternatively, the heat source and light source may comprise different types of light emitting diodes (LEDs) arranged in an array on a probe (14) disposed at the treatment site. Also mounted on the fixture is a temperature sensor (30), which produces a signal indicative of the temperature at the treatment site. In response to this signal, a controller (24/36) controls the heat source to prevent vascular damage. In addition to enhancing the perfusion of a photoreactive agent into the treatment site, heating the tissue at the site prior to initiating the PDT greatly enhances the efficacy of this treatment.

27 Claims, 3 Drawing Sheets

METHOD AND DEVICE FOR APPLYING HYPERTHERMIA TO ENHANCE DRUG PERFUSION AND EFFICACY OF SUBSEQUENT LIGHT THERAPY

FIELD OF THE INVENTION

The present invention generally relates to a device and a procedure for applying heat to tissue, and more specifically, to the use of this device and procedure for enhancing the effects of a medical treatment that depends upon the perfusion of a reagent into the tissue.

BACKGROUND OF THE INVENTION

Abnormal tissue in the body is known to selectively absorb certain dyes perfused into a treatment site to a much greater extent than surrounding tissue. For example, tumors of the pancreas and colon may absorb two to three times the volume of certain dyes, compared to normal tissue. Once pre-sensitized by dye tagging, the cancerous or abnormal tissue can be destroyed by irradiation with light of an appropriate wavelength or waveband corresponding to an absorbing wavelength or waveband of the dye, with minimal damage to normal tissue. This procedure, which is known as photodynamic therapy (PDT), has been clinically used to treat metastatic breast cancer, bladder cancer, lung carcinomas, esophageal cancer, basal cell carcinoma, malignant melanoma, ocular tumors, head and neck cancers, and other types of malignant tumors. Because PDT may selectively destroy abnormal tissue that have absorbed more of the dye than normal tissue, it can successfully be used to kill malignant tissue with less effect on surrounding benign tissue than alternative treatment procedures.

Typically, invasive applications of PDT are used during surgical procedures employed to gain access to a treatment site inside the body of the patient to administer light produced by relatively high intensity light sources, such as high power lasers or solid state laser diode (LD) arrays. Optical fibers in a hand-held probe are often used to deliver the intense light to the surgically exposed treatment site from a remote laser source to reduce damage to surrounding tissue from the heat developed by the laser source.

It has been shown possible, in certain cases, to obtain improved therapeutic results in PDT at a low light level. As reported by J. A. Parrish in "Photobiologic Consideration in Photoradiation Therapy," pp. 91–108, *Porphyrin Photosensitization*, Plenum Press, (1983), preliminary laboratory studies with hematoporphyrin and visible light suggest that low intensity light may be more effective in PDT. In these experiments, subcutaneous tumors in the flanks of newborn rats were treated with the same external dose of 620 nm radiation, at intensities of 7.5, 28, and 75 mW/cm$^2$. At the same total light dosage, Parrish found that greater tumor necrosis occurred at the lowest light intensity used.

Light emitting probes designed to be transcutaneously introduced into the body of a patient at a desired treatment site, to administer PDT using low light level sources, for extended periods of time, are taught in commonly assigned U.S. Pat. No. 5,445,608, the drawings and disclosure of which are specifically incorporated herein by reference. Several different embodiments of such probes are illustrated and discussed in this patent. Each of the probes disclosed in this reference includes a plurality of light sources that are mounted on a substrate and enclosed within a transparent envelope through which light emitted by the light sources is transmitted to the tumor or other cells to be destroyed by PDT. The light sources used on the probes taught by this reference are preferably light emitting diodes (LEDs). By transcutaneously inserting one of these probes into an internal treatment site and applying PDT over an extended time frame, abnormal tissue at the treatment site can be destroyed without adverse impact on normal tissue.

U.S. Pat. No. 5,445,608 discloses that a light source on a probe implanted at a treatment site within a patient's body will give off heat that increases the temperature of the abnormal tissue at the treatment site. An increase in the efficacy of PDT is thus achieved due to the elevated temperature of the tissue. Other beneficial effects of hyperthermia are known in the prior art. For example, hyperthermia has been utilized to enhance permeation of various medicaments into the tissue comprising a tumor. It is believed that an increase in blood flow in the tissue subject to hyperthermia and/or an enlargement of endothelial gaps within the tumor vessels may be responsible for enhanced drug delivery to a tumor site. Another beneficial use of hyperthermia applied to a tumor site is to split heat sensitive liposomes containing antitumor agents, and thus, to provide selective drug delivery to the site.

Abnormal tissue in a tumor differs from normal tissue in its resistance to the perfusion of medicaments. In addition, as any treatment of a tumor begins to destroy cells on the surface of the tumor, the necrotic cell layer resulting from the treatment tends to resist infusion of medicaments to the underlying live abnormal tissue. It would thus be desirable to enhance the perfusion of medicament fluids such as photoreactive reagents into the tissue of the tumor that will subsequently be destroyed by PDT. Further, it would be desirable to enhance the efficiency of PDT without the need for additional hardware to be inserted into the treatment site beyond that necessary to administer PDT. The present invention addresses these objectives.

SUMMARY OF THE INVENTION

In accord with the present invention, a method for increasing the perfusion of a drug through tissue at a treatment site where photodynamic therapy is to be administered comprises the step of positioning a fixture that emits light adjacent to the treatment site for use in administering the photodynamic therapy. The fixture includes means for providing heat to the tissue at the treatment site to raise its temperature. The drug is then delivered to the treatment site. The elevated temperature of the tissue caused by the heat that was supplied increases the perfusion of the drug through the tissue at the treatment site to enhance the effect of the drug on the tissue.

In the preferred embodiment of the invention, the drug comprises a photoreactive reagent. A light source provided on the fixture is used to irradiate the tissue at the treatment site after the perfusion of the photoreactive agent through the tissue has been enhanced by heating the tissue, to administer the photodynamic therapy.

The fixture preferably includes a first light source that emits light having a first waveband, which substantially overlaps a characteristic absorption waveband of the drug delivered to the tissue at the treatment site and which is energized to administer the photodynamic therapy. A second light source on the fixture emits light having a second waveband substantially different from the first waveband. The second light source comprises the means for heating, where the second waveband of the light emitted by the second light source heats the tissue, but generally are not used to implement PDT. The first and second light sources preferably comprise an array of light emitting solid state devices.

Another step of the method provides for monitoring a temperature of the tissue at the treatment site, producing a signal indicative of the temperature. The means for providing heat are then controlled in response to the signal indicative of the temperature of the tissue at the treatment site, so that the temperature does not exceed a level likely to cause vascular damage.

In one preferred embodiment, the treatment site is internal to a patient's body, and the fixture is disposed at the internal treatment site to provide heat and to administer the photodynamic therapy. The fixture of this embodiment comprises a probe that is adapted to be left within the patient's body for an extended period of time while PDT is administered. In another use of the present invention, the drug that infuses throughout the heated tissue is employed for a medical treatment other than PDT.

Instead of using a light source to produce heating of the treatment site, a resistive element can be employed to generate heat. The resistive element can be coupled to a power source using conductors that are separate from those supplying power to the light source used for PDT so that the light source and resistive element can be separately controlled.

An alternative embodiment uses a light source for both PDT and as the means for heating the treatment site. In this embodiment of the invention, the light source can be activated prior to administration of the drug, to heat the treatment site, and then de-energized. After the drug is administered, the light source is again activated to provide the light required for PDT.

In addition to enhancing the perfusion of the drug in tissue at the treatment site, heat applied to the treatment site can be used to release the drug from a drug carrier. Heat sensitive drug carriers such as liposomes and polymers are usable for this purpose.

Another aspect of the present invention is directed to an apparatus for increasing a perfusion of a drug through tissue at a treatment site where PDT is to be administered. The apparatus generally includes components that implement functions consistent with the steps and other details of the method described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1:
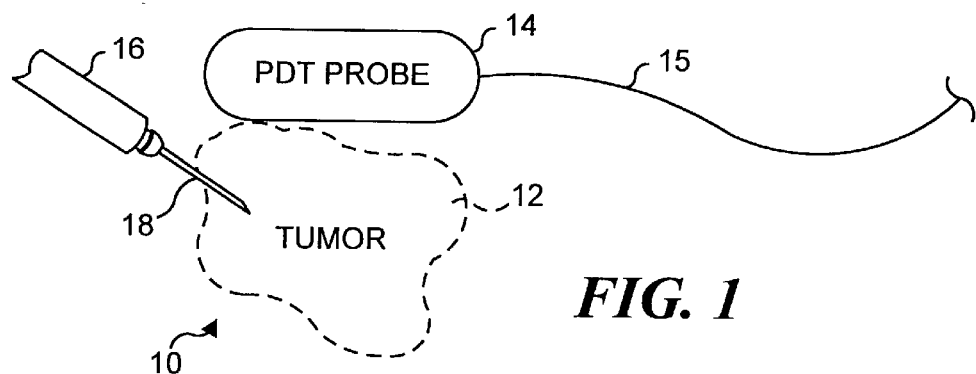
FIG. 1 is a schematic view showing a tumor, a PDT probe, and a portion of a syringe that is being used to inject a drug into the tumor.

A treatment site 10 within a patient's body (not otherwise shown) is schematically illustrated in FIG. 1. At treatment site 10, a tumor 12 comprising cancerous or other abnormal tissue having a generally amorphous shape is illustrated by a dashed line. The present invention is intended for applying medical treatment to tumor 12 with the expectation that the abnormal tissue will be killed thereby, eliminating the tumor or at least substantially reducing its size. As explained above in the Background of the Invention, and in much greater detail in U.S. Pat. No. 5,445,608, which has been incorporated herein, a PDT probe 14 can be implanted within a patient's body at treatment site 10 to deliver PDT for an extended period of time. PDT probe 14 includes a plurality of solid state light sources, such as light emitting diodes (LEDs), laser diodes, electroluminescent devices, resistive filament lamps, or vertical cavity surface emitting lasers (VCSELs), which are not separately shown in FIG. 1. To effect PDT, a photoreactive agent is infused into the abnormal tissue comprising tumor 12. Since the photoreactive agent is preferentially absorbed by the abnormal tissue rather than by the surrounding normal tissue, the effect of PDT on the abnormal tissue of the tumor is substantially more pronounced than its effect on the surrounding normal tissue.

In FIG. 1, a syringe 16 coupled to a needle 18 is illustrated in a position for infusing the photoreactive agent into tumor 12. It is also contemplated that the photoreactive agent can be delivered to tumor 12 in other ways, such as by a general infusion of the reagent into a patient's vascular system, orally, or by delivery through a lumen of a catheter coupled to PDT probe 14; the electrical leads attached to probe 14 are generally represented by a line 15 in FIG. 1. Alternatively, a heat sensitive drug carrier such as a liposome or a polymer can carry the drug to the treatment site so that when the treatment site is heated by the PDT probe, the drug carrier releases the drug into the treatment site so that the drug infuses throughout the tissue at the site.

Figure 2:
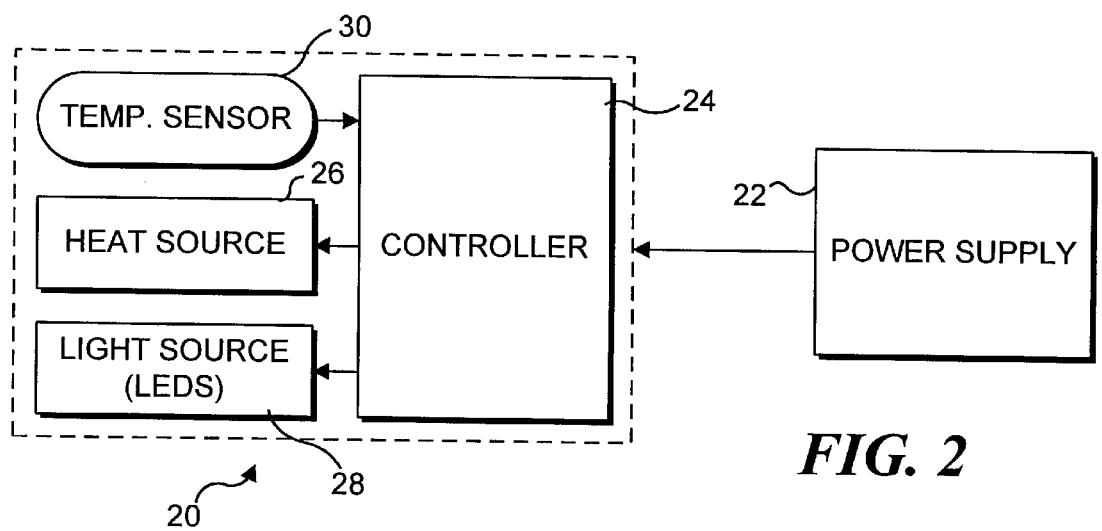
FIG. 2 is a schematic block diagram of a first embodiment of the present invention, showing an implantable fixture having a separate heat source and light source for respectively applying heat and PDT to an internal treatment site, a controller, and a temperature sensor for monitoring the temperature of tissue at the treatment site.
Figure 3:
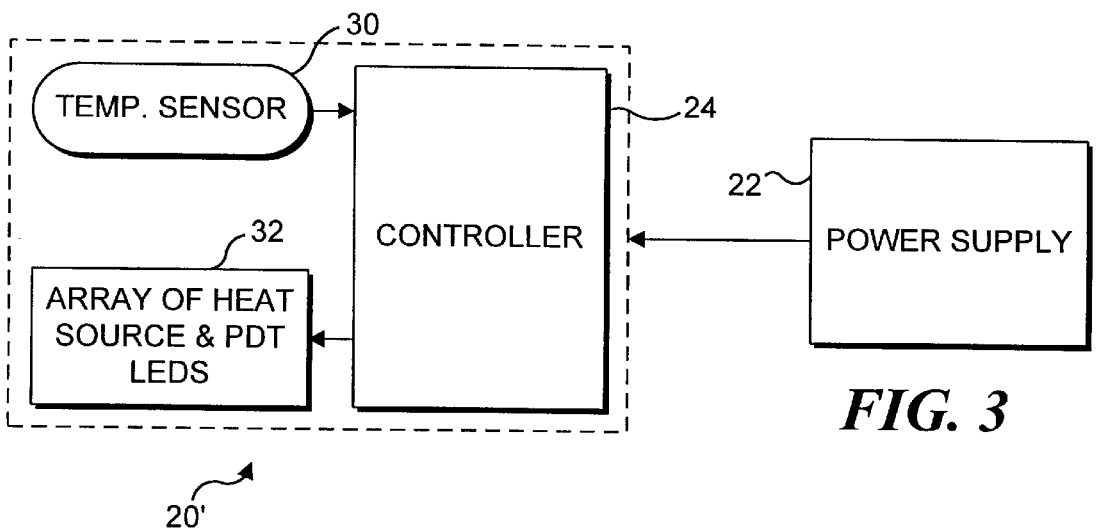
FIG. 3 is a schematic block diagram of a second embodiment of the present invention, which is similar to that of FIG. 2, except that the heat source and light source comprise an array of LEDs.
Figure 4:
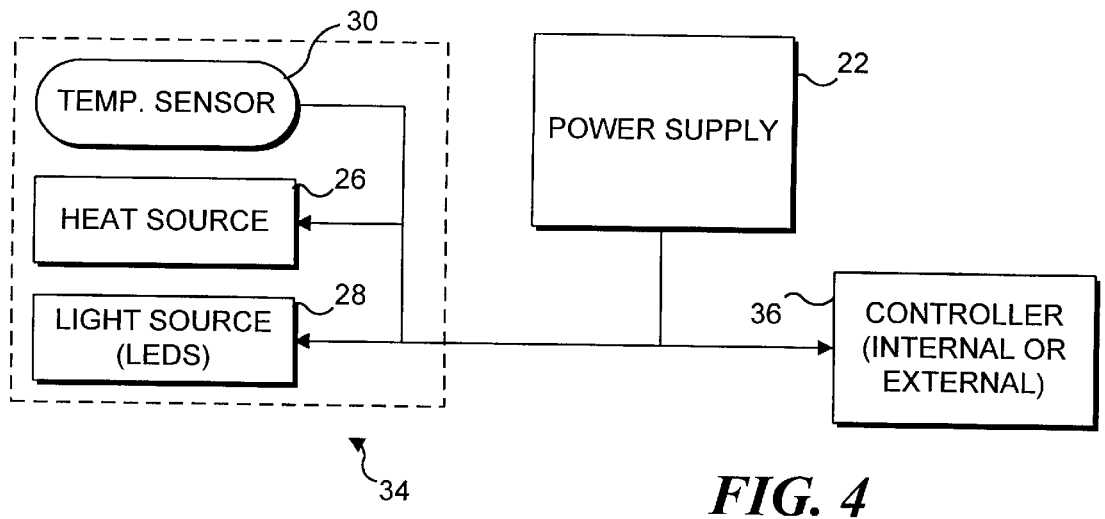
FIG. 4 is a schematic block diagram of a third embodiment of the present invention, which is similar to the first, except that the controller is separate from the fixture.
Figure 5:
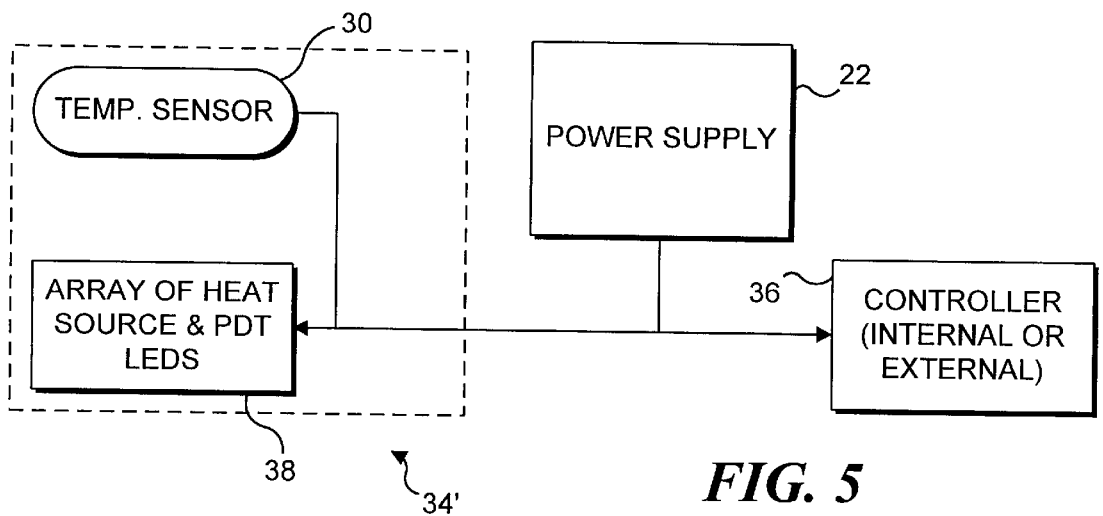
FIG. 5 is a schematic block diagram of a fourth embodiment of the present invention, which is similar to the second embodiment, except that the controller is separate from the fixture.

In connection with the present invention, PDT probe 14 comprises a fixture, such as fixture 20 as shown in FIG. 2. This fixture may have several different configurations or embodiments, others of which are illustrated in FIGS. 3–5. In the first embodiment shown in FIG. 2, fixture 20 is coupled to a power supply 22 Power supply 22 may comprise a battery source, which is disposed within the patient's body, either at the same site as the PDT probe, or at a different location. Alternatively, power supply 22 may be disposed externally, and coupled through leads 15 to the PDT probe. It is also contemplated that if disposed internally, electrical power may be transferred from outside the patient's body to the power supply using a source of infrared light that passes readily through the dermal layer of a patient's body. The infrared light is thus received by a photovoltaic transducer (not shown) disposed within the patient's body. Alternatively, power may be supplied from an external source using an electromagnetic field. In this approach, an external coiled conductor, which is energized from an alternating current (AC) or pulsating direct current (DC) source can electromagnetically couple power to a conductor coil disposed within the patient's body. The power thus supplied can be used directly or for charging a storage battery disposed within power supply 22. Further details concerning the various alternatives usable to energize power supply 22 are not discussed herein, since they do not directly relate to the present invention.

A controller 24 in the first embodiment of fixture 20 is connected to a heat source 26 and to a separate light source 28. Preferably, light source 28 comprises a plurality of LEDs; however, it is also contemplated that other types of solid state light sources such as laser diodes, VCSELs, filament lamps, or electroluminescent devices can be used instead. Light source 28 emits the light that is employed for PDT after the photoreactive agent is infused into the abnormal tissue comprising tumor 12. Accordingly, light emitted by light source 28 has a characteristic waveband corresponding to an absorption waveband of the photoreactive agent.

In this embodiment, heat source 26 comprises either a light source or a resistance element that produces heat due to the flow of an electrical current through the device. Although a separate heat source is illustrated, light source 28 can instead be used to both provide heating of the treatment site and supply light to implement PDT. Thus, the light source can be initially energized to heat the treatment site, then de-energized until after the drug is administered, and re-energized to provide light of the required waveband to effect the PDT. However, it is preferable to use heat source 26 separate from light source 28, since more versatile control of the two sources is then possible. Unlike light source 28, heat source 26 emits energy within a waveband that is substantially different than the absorption waveband of the photoreactive agent. Instead, the waveband of energy emitted by the heat source is suitable for supplying heat to tissue at the treatment site.

Increasing the temperature of the tissue at the treatment site provides several benefits in connection with administering PDT. Specifically, the elevated temperature of the tissue caused by energy emitted from heat source 26 is believed to cause an increase in the flow of blood, both in the normal tissue surrounding tumor 12, and in the vascular system of the tumor itself. The increased flow of blood is believed to enhance the perfusion of the photoreactive agent or other drug that is injected into the abnormal tissue at the treatment site.

The preheating of the treatment site to a temperature less than 40° C. for a time interval of from 20–60 minutes prior to administering PDT is optionally combined with heating of the treatment site after (or while) PDT is administered. The elevated temperature of the tissue in tumor 12 prior to administering PDT is believed to enhance the effects of PDT by increasing drug uptake into the abnormal tissue at the treatment site, substantially improving the efficacy of the therapy. Thus, more abnormal tissue is killed for a given exposure time, compared to the result that would be obtained absent preheating of the tissue at the treatment site. It is expected that substantial further benefits can be achieved after PDT is administered, by heating the treatment site to a temperature in the range of 40°–45° C. for a time interval of from 20–60 minutes. The time and temperature parameters for any hyperthermia treatment applied, before, during, and after PDT is administered will likely vary depending upon the type of abnormal tissue being treated, the power dissipated by the heat source, the type of drug being infused into the treatment site, and other variables. Thus, more specific values for these variables will depend upon empirical clinical results yet to be determined.

To avoid heating normal tissue to a level that might cause vascular damage, a temperature sensor 30 is provided in fixture 20 to monitor the temperature at the treatment site. Temperature sensor 30 produces a signal in response to the temperature of the tissue that is input to controller 24. Controller 24 in turn controls an electrical current supplied to energize heat source 26 to maintain the temperature at a set point and/or to prevent the temperature of the tissue from exceeding a predefined level at which vascular damage might be expected.

Figure 7:
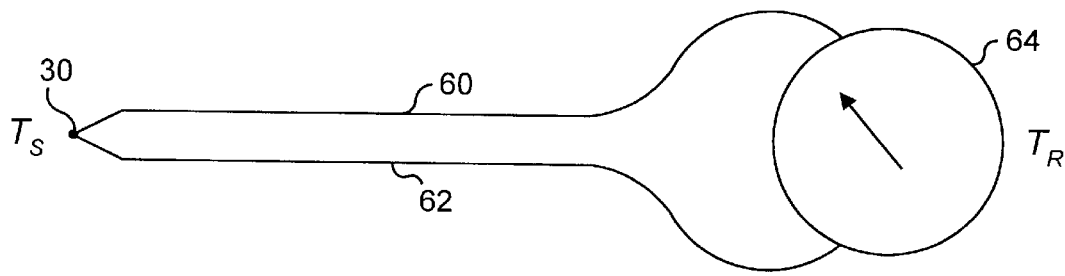
FIG. 7 is a schematic diagram of a thermocouple used for a temperature sensor to monitor the temperature of tissue at the treatment site.

FIG. 7 illustrates a preferred embodiment of temperature sensor 30, wherein the temperature sensor comprises a thermocouple that is disposed on the fixture. Temperature sensor 30 is coupled through leads 60 and 62 to a reference junction 64, which preferably simulates a predefined temperature, such as the ice point (0° C.) of water. The voltage differential between temperature sensor 30, which is exposed to a temperature $T_S$, and the reference point, which is nominally at a reference temperature $T_R$, is indicative of the temperature sensed by temperature sensor 30. It is also contemplated that other types of temperature sensors, such as a resistance temperature device, or a thermistor could be used instead of a thermocouple junction for monitoring the temperature at the treatment site. These and other types of temperature sensors are well known to those of ordinary skill in the art.

After applying heat to the tumor for a predefined period of time, e.g., for 20–60 minutes or sufficiently long to achieve a desired temperature rise at the site, as determined by temperature sensor 30, heat source 26 is de-energized by controller 24. Either during or after heating of the abnormal tissue in tumor 12 and the surrounding tissue, the photoreactive agent is injected into tumor 12. As noted above, the increased temperature of the abnormal tissue comprising the tumor increases the perfusion of the photoreactive agent throughout the tumor. Controller 24 deactivates heat source 26 and activates light source 28 to effect PDT in a sequence that depends upon the particular type of protocol desired. As noted above, the heat source can be selectively energized to heat the tissue at the treatment site, before, during, and/or after PDT is administered.

Following administration of PDT, heat is applied to the treatment site for an appropriate time, e.g., for 20–60 minutes, so as to elevate the temperature of the treatment site to a desired level, e.g., 40°–45° C. for a desired time, e.g., 20–60 minutes. The efficacy of the PDT treatment or other drug therapy is improved because of the elevated temperature of the treatment site. It may also be desirable to apply heat to the treatment site during PDT to further improve the efficacy of the therapy.

In the preferred embodiment, PDT probe 14 is designed to be left in place within the patient's body for an extended period of time, during which PDT is conducted. However, it is also contemplated that other types of PDT probes may be used that are not designed to be implanted. Such probes will include a substantially higher intensity light source to effect PDT during a shorter period of time, e.g., while an internal treatment site is exposed during a surgical procedure, or to an external treatment site. For some types of tumors, it is possible that even a relatively low intensity light source can have the required effect upon the abnormal tissue as a result of the improvements achieved by applying heat to the treatment site. Accordingly, such a probe might effectively be used during a surgical operation, while the treatment site is exposed. In contrast, an implantable probe is designed to be left in place within a patient's body at the treatment site. The implantable probe may be placed endoscopically or while the treatment site is exposed by an incision.

Referring now to FIG. 3, a second embodiment of a fixture 20' is shown. Fixture 20' is identical to fixture 20, except that on fixture 20', the heat source and light source are combined and comprise an array of heat emitting and PDT LEDs 32. Controller 24 is coupled to this array and determines whether the heat emitting LEDs or PDT LEDs are energized. The heat emitting LEDs preferably emit light in the infrared waveband. Again, temperature sensor 30 provides a signal indicative of the temperature at the treatment site for purposes of controlling the heat source LEDs and for preventing an excessive temperature rise at the treatment site, which might cause vascular damage to the normal tissue surrounding the tumor.

Figure 8:
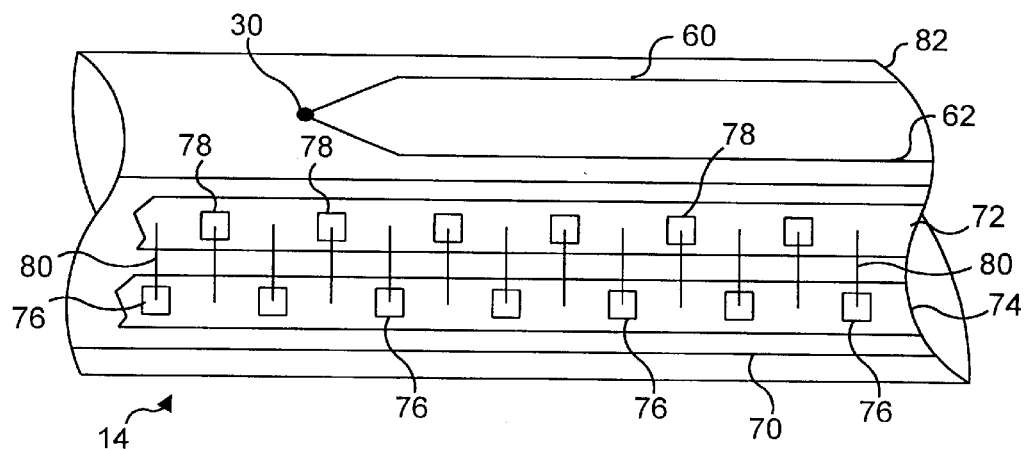
FIG. 8 is a schematic block diagram showing a portion of an implantable probe in accord with the present invention.

Referring to FIG. 8, further details of PDT probe 14 are illustrated, showing heat source LEDs 76 and PDT LEDs 78 enclosed in a transparent biocompatible envelope 82. In this probe, an elongate substrate strip 70 includes two parallel conductive traces 72 and 74 formed on a surface thereof. A plurality of heat source LEDs 76 are arranged in a spaced-apart array, so that the cathodes of each of the LEDs comprising the heat source are coupled electrically to conductive trace 74. Aluminum flywires 80 (or other conductors) are connected to the anode of each of the LEDs comprising the heat source and extend over to conductive traces 72, where they are electrically coupled. Similarly, PDT LEDs 78 have their cathodes electrically mounted on conductive trace 72 and an aluminum flywire 80 extends from the anode of each of the PDT LEDs to connect electrically to conductive trace 74. Depending upon the polarity of DC voltage applied across conductive traces 72 and 74 by controller 24, either the heat source LEDs or PDT LEDs will be energized. However, it will be apparent that only one of these two types of LEDs is energized at a time, based upon the polarity of the DC voltage applied to the two conductive strips. Thus, controller 24 initially energizes the heat source LEDs to heat the treatment site to the desired temperature, and then changes the polarity applied to conductive traces 72 and 74 to de-energize the heat source LEDs and energize the PDT LEDs. Those of ordinary skill in the art will appreciate that other techniques for selectively energizing the heat source and PDT LEDs can be used besides the approach used in this preferred embodiment. For example, separate pairs of conductive traces may be coupled to the heat source LEDs and to the PDT LEDs so that by selectively applying the appropriate DC voltage to the conductive traces connected to either the heat source LEDs or PDT LEDs, the controller can selectively control the types of LEDs energized at any given time. Further, if an AC voltage is applied to the probe, both sets of LEDs will be energized, one set by the positive waveform and the other set of LEDs by the negative waveform. Each set of LEDs (or each set of other types of light emitting devices) can be independently controlled to emit light of selected magnitude by independently controlling the magnitude or duration of the positive and negative waveform portions of the AC voltage applied thereto, as will be understood by those of ordinary skill in the art. Pulsed DC voltage can also be applied to independently control the intensity of each set of LEDs or other light sources as a function of the duty cycle of the respective positive and negative DC pulses.

In FIG. 4, a fixture 34 is illustrated that differs from fixture 20 because a controller 36 is separate from fixture 34 instead of being included on it. Specifically, controller 36 is either disposed at a separate location internally within the patient's body, or is coupled to the fixture through leads that extend externally of the patient's body. In all other respects, fixture 34 is identical to fixture 20. By moving controller 36 to a point separate from fixture 34, the size of the fixture may be reduced, since the elements comprising controller 36 need not be fitted within the fixture.

A fixture 34' is shown in FIG. 5 that is identical to fixture 20' in FIG. 3, except that a controller 36 is not included in fixture 34' with the temperature sensor and array of heat source and PDT LEDs. The same comments regarding controller 36 apply in connection to the embodiment of FIG. 5.

Figure 6:
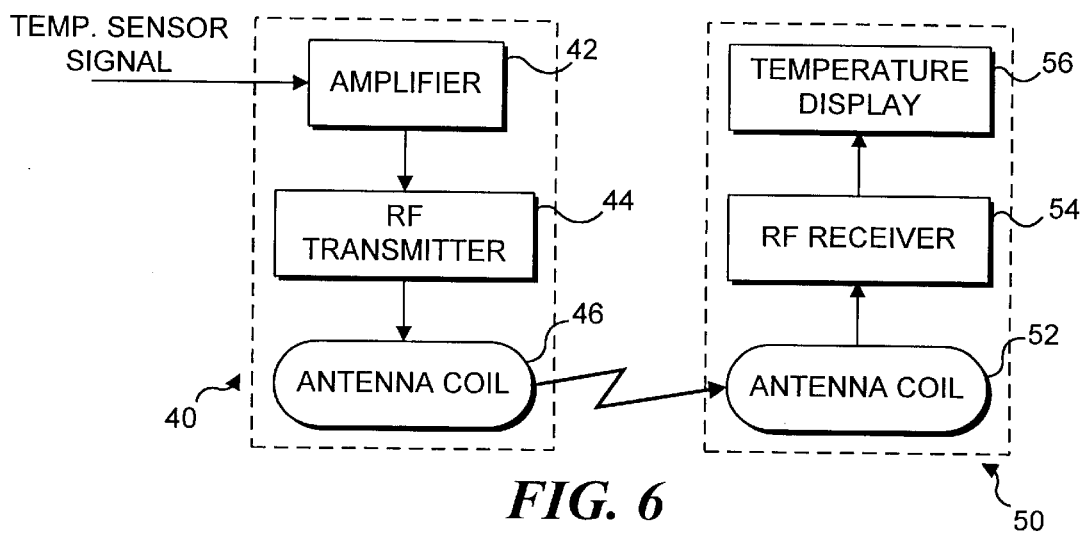
FIG. 6 is a schematic block diagram of a data transmitter and receiver for transmitting a temperature signal to an external monitor.

In FIG. 6, details of a data transmitting section 40 of the controller that is optionally used for transmitting a temperature telemetry signal from inside the patient's body and details of an external receiving section 50 for receiving the telemetry signal are shown. When data transmitting section 40 is employed, the temperature sensor signal produced by temperature sensor 30 is input to an amplifier 42, which amplifies the signal, increasing its voltage. The amplified signal from amplifier 42 is input to a radio frequency (RF) transmitter 44, where it is used to modulate an RF signal that is transmitted by an antenna coil 46. The signal transmitted by antenna coil 46 comprises the temperature telemetry data signal that is picked up by an antenna coil 52 in receiving section 50, which is disposed outside the patient's body. An RF receiver 54 demodulates the signal from antenna coil 52, recovering the temperature at the treatment site. This temperature appears on a temperature display 56 so that it can be monitored by a physician or other medical personnel. As a further option, it may be desirable for the physician to be able to transmit a signal back to the controller to modify the set point limit used in controlling the heat source. To enable that option, the controller must also be provided with a receiver section and must respond to an externally transmitted signal that modifies the set point limit.

Figure 6A:
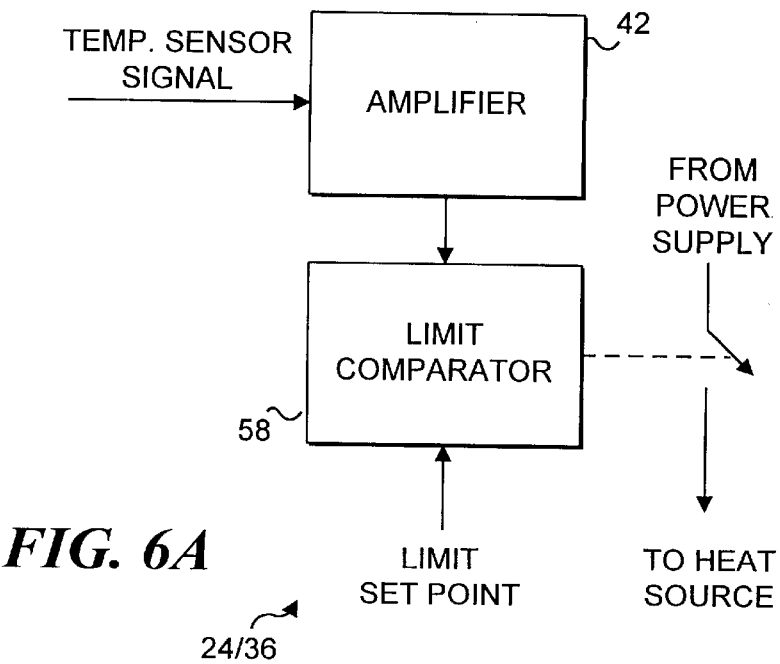
FIG. 6A is a schematic block diagram of the controller.

In FIG. 6A, further details of controller 24/36 are illustrated. Amplifier 42 is again used to amplify the temperature sensor signal, increasing its voltage. The amplified signal from amplifier 42 and a predetermined limit set point are input to a limit comparator 58. If the temperature of the tissue at the treatment site exceeds the limit set point, limit comparator 58 de-energizes the heat source/heat source LEDs by interrupting the electrical current from the power supply to protect the normal tissue adjacent the treatment site from harm due to overheating. As those of ordinary skill in the art will understand, a more sophisticated temperature control scheme (not shown) can be used in place of the limit comparator to continuously maintain the temperature of the tissue at the treatment site at a desired set point level.

In addition to improving the perfusion of a photoreactive agent into the treatment site, it is also contemplated that the heat applied to a treatment site prior to initiating PDT can be used to improve the rate at which other types of drugs are perfused throughout the treatment site. Such drugs might presensitize the tumor site to enhance PDT or may improve the binding of the photoreactive agent to the abnormal tissue at the treatment site. Examples of drugs that might be used include heat sensitive liposomes and antibody conjugates.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for increasing a perfusion of a drug through tissue at a treatment site where photodynamic therapy is to be administered, comprising the steps of:
   a) positioning a probe having thereon a light emitting means for administering photodynamic therapy so that the probe is disposed adjacent to the treatment site, said probe further including means thereon for providing heat separate from said light emitting means;
   b) energizing the means for providing heat to supply heat to the tissue at the treatment site without energizing the light emitting means, said heat raising the temperature of the tissue; and
   c) delivering the drug to the tissue at the treatment site, an elevated temperature of the tissue caused by the heat increasing the perfusion of the drug through the tissue at the treatment site to enhance an effect of the drug on the tissue.

2. The method of claim 1, wherein the drug comprises a photoreactive agent, further comprising the step of supplying light from a light source on the fixture to irradiate the tissue at the treatment site after the perfusion of the photoreactive agent through the tissue has been increased by heating the tissue, said light being used to administer the photodynamic therapy.

3. The method of claim 2, wherein the probe includes:
   (a) a first light source that is adapted to emit a light having a first waveband that substantially overlaps a characteristic absorption waveband of the drug delivered to the tissue at the treatment site, said first light source being energized to administer the photodynamic therapy; and
   (b) a second light source that is adapted to emit a light having a second waveband substantially different from the first waveband, said second light source comprising the means for providing heat, the light emitted by the second light source thus heating the tissue, but generally not effecting the photodynamic therapy.

4. The method of claim 1, wherein the probe includes a plurality of light sources, said means for providing heat comprising at least a portion of the light sources.

5. The method of claim 1, further comprising the steps of:
   (a) monitoring a temperature of the tissue at the treatment site, producing a signal indicative of the temperature;
   (b) controlling the means for providing heat in response to the signal indicative of the temperature of the tissue at the treatment site so that said temperature does not exceed a level that would cause vascular damage at the treatment site.

6. The method of claim 1, wherein the treatment site is internal to a patient's body and the probe is disposed at the internal treatment site to provide heat and administer the photodynamic therapy, said fixture comprising a probe that is adapted to be left within the patient's body for an extended period of time, while the photodynamic therapy is administered.

7. The method of claim 1, wherein the drug is used for a medical treatment other than the photodynamic therapy.

8. The method of claim 1, wherein the means for providing heat comprise a resistance heating element that produces heat in response to an electrical current flowing through the resistance element.

9. The method of claim 1, wherein the treatment site is heated to an elevated temperature prior to delivering the drug to the tissue at the treatment site.

10. The method of claim 1, wherein the drug is carried to the treatment site by a heat sensitive drug carrier that releases the drug when the treatment site is heated to an elevated temperature.

11. Apparatus for increasing a perfusion of a drug through tissue at a treatment site where photodynamic therapy is to be administered, comprising:
    a) a probe configured to be placed at the treatment site having means thereon for emitting light; and
    b) said probe having means for heating the tissue at the treatment site separate from said light emitting means to increase the perfusion of the drug into the tissue, said means for heating being disposed on the probe; and
    c) a controller connected to said light emitting means which allows the light emitting means to be energized without energizing the heating means.

12. The apparatus of claim 11, further comprising a light source disposed on the fixture, wherein the treatment site is disposed internally of a patient's body, and wherein the probe is adapted to be inserted internally of the patient's body at the treatment site, said light source being capable of emitting a light that is directed toward the tissue at the treatment site to effect the photodynamic therapy.

13. The apparatus of claim 12, wherein the light source comprises a plurality of light emitting devices mounted to the fixture, at least a portion of said light emitting devices being adapted to produce a light having a waveband corresponding to a characteristic absorption waveband of a photoreactive agent comprising the drug.

14. The apparatus of claim 13, wherein the means for heating the tissue comprise a plurality of light emitting devices that are mounted to the probe and produce light having a waveband substantially different than the characteristic absorption waveband of the photoreactive agent.

15. The apparatus of claim 14, wherein the means for heating and the light source are each selectively separately controlled.

16. The apparatus of claim 11, wherein the means for heating comprise a plurality of light emitting devices arranged in a spaced-apart array.

17. The apparatus of claim 11, further comprising a temperature sensor disposed on the probe, said temperature sensor being adapted to produce a signal indicative of a temperature of the tissue at the treatment site.

18. The apparatus of claim 17, further comprising means for controlling the means for heating in response to the signal indicative of the temperature, so that the temperature of the tissue does not exceed a level that causes vascular damage.

19. The apparatus of claim 18, wherein the means for controlling are adapted to be disposed internally of a patient's body.

20. The apparatus of claim 18, wherein the means for controlling are adapted to be disposed externally of a patient's body.

21. The apparatus of claim 18, further comprising a transmitter coupled to the probe to receive the signal produced by the temperature sensor for transmission as a wireless telemetry signal from inside the patient's body.

22. The apparatus of claim 21, further comprising a receiver disposed outside the patient's body, said receiver being adapted to receive the wireless telemetry signal and display the temperature of the tissue.

23. The apparatus of claim 18, wherein the means for controlling are coupled to the temperature sensor via a lead that extends from the fixture and is disposed inside the patient's body.

24. A method for increasing an efficacy of a photodynamic therapy, comprising the steps of:
   a) applying a photoreactive agent to a treatment site, said photoreactive agent having a characteristic absorption waveband;
   b) energizing a light generating device and directing light generated the toward the treatment site from a probe used to administer the photodynamic therapy, said light having a waveband substantially corresponding to the characteristic absorption waveband of the photoreactive agent; and
   c) heating the treatment site after terminating the delivery of light from the light generating device using a heat source that is disposed on said probe, thereby raising the temperature of the treatment site to increase the efficacy of the photodynamic therapy.

25. The method of claim 24, wherein the heat source comprises a source of light that is not used for administering the photodynamic therapy.

26. The method of claim 24, wherein the heat source comprises a resistive heating device.

27. The method of claim 24, further comprising the steps of:
   (a) monitoring a temperature of the treatment site, producing a signal indicative of the temperature;
   (b) controlling heat source in response to the signal indicative of the temperature of the treatment site so that said temperature does not exceed a level that would cause vascular damage.

* * * * *

UNITED STATES PATENT AND TRADEMARK OFFICE
CERTIFICATE OF CORRECTION

PATENT NO. : 5,814,008
DATED : September 29, 1998
INVENTOR(S) : Chen et al.

It is certified that error appears in the above-identified patent and that said Letters Patent is hereby corrected as shown below:

On the title page,

Section [56], Other Publications, 5th Reference   "Hypethermia" should read --Hyperthermia--

Section [57], Abstract, Line 1   "beat" should read --heat--

Column 11, Line 11 (Claim 24, Line 7)   "the" (first occurrence) should read --thereby--

Signed and Sealed this

Twenty-fifth Day of May, 1999

Attest:

Q. TODD DICKINSON

Attesting Officer   Acting Commissioner of Patents and Trademarks